(12) United States Patent
O'Hara

(10) Patent No.: US 10,898,528 B2
(45) Date of Patent: *Jan. 26, 2021

(54) **COMPOSITION COMPRISING *LACTOBACILLUS PLANTARUM* 2830 (ECGC 13110402)**

(71) Applicant: OPTIBIOTIX LIMITED, Yorkshire (GB)

(72) Inventor: Stephen Patrick O'Hara, Yorkshire (GB)

(73) Assignee: Optibiotix Limited, Yorkshire ( * ) Notice: Subject to any disclaimer, the term of this patent is extended or adjusted under 35 U.S.C. 154(b) by 126 days.

This patent is subject to a terminal disclaimer.

(21) Appl. No.: 15/764,970

(22) PCT Filed: Nov. 2, 2016

(86) PCT No.: PCT/GB2016/053389
§ 371 (c)(1),
(2) Date: Mar. 30, 2018

(87) PCT Pub. No.: WO2017/077285
PCT Pub. Date: May 11, 2017

(65) Prior Publication Data
US 2018/0318364 A1    Nov. 8, 2018

(30) Foreign Application Priority Data
Nov. 2, 2015 (GB) .................... 1519326.1

(51) Int. Cl.
| | | |
|---|---|---|
| *A61K 35/747* | (2015.01) | |
| *A61K 35/74* | (2015.01) | |
| *A61P 9/00* | (2006.01) | |
| *A61K 9/19* | (2006.01) | |
| *A61K 45/06* | (2006.01) | |
| *A61K 47/02* | (2006.01) | |
| *A61K 47/12* | (2006.01) | |
| *A61K 47/26* | (2006.01) | |
| *A61K 47/36* | (2006.01) | |
| *C12R 1/25* | (2006.01) | |

(52) U.S. Cl.
CPC .............. *A61K 35/747* (2013.01); *A61K 9/19* (2013.01); *A61K 35/74* (2013.01); *A61K 45/06* (2013.01); *A61K 47/02* (2013.01); *A61K 47/12* (2013.01); *A61K 47/26* (2013.01); *A61K 47/36* (2013.01); *A61P 9/00* (2018.01); *C12R 1/25* (2013.01)

(58) Field of Classification Search
CPC ........ A61K 35/747; A61K 9/19; A61K 47/02; A61K 47/36; A61K 47/26; A61K 35/74; A61K 45/06; A61K 47/12; C12R 1/25; A61P 9/00

See application file for complete search history.

(56) References Cited

U.S. PATENT DOCUMENTS

| | | | | |
|---|---|---|---|---|
| 2003/0039723 A1* | 2/2003 | Park | ........................ | A23L 2/38 426/28 |
| 2012/0213753 A1* | 8/2012 | Cune Castellana | .... | A61K 35/74 424/93.45 |
| 2014/0065114 A1* | 3/2014 | Lin | ..................... | A61K 35/747 424/93.45 |

FOREIGN PATENT DOCUMENTS

WO    2015149818 A1    10/2015

* cited by examiner

*Primary Examiner* — Satyendra K Singh
(74) *Attorney, Agent, or Firm* — Davis, Brown, Koehn, Shors & Roberts, P.C.; Sean D. Solberg

(57) ABSTRACT

The present invention relates to compositions comprising *Lactobacillus plantarum* 2830 (ECGC 13110402), or mutant strain or strains thereof, for use in the treatment or prevention of hypercholesterolaemia, and in particular reducing the total cholesterol (TC) and low density lipoprotein cholesterol (LDL-C) levels, in an individual. Specific dosage regimes and methods of production are also claimed and described.

18 Claims, No Drawings

COMPOSITION COMPRISING *LACTOBACILLUS PLANTARUM* 2830 (ECGC 13110402)

TECHNICAL FIELD OF THE INVENTION

The invention relates to compositions comprising *Lactobacillus plantarum* 2830 (ECGC 13110402) for use in the treatment, prevention or control of cholesterol.

BACKGROUND TO THE INVENTION

Cardiovascular disease (CVD) is a leading cause of death globally. The World Health Organisation (WHO) predicts that by the year 2020, up to 40% of all human deaths will be related to CVD. Elevated blood cholesterol levels, in particular raised levels of low density lipoprotein cholesterol (LDL-C), are known risk factors for CVD and coronary artery disease (CAD). Therefore therapies for the reduction and control of cholesterol levels and specifically LDL-C levels are being researched intensively.

The majority of cholesterol-lowering therapies currently used are statins. However, statins have a range of intolerance and safety concerns which affect compliance and they are expensive. Plant sterols and stanols have been explored as possible alternatives to statins. However large amounts of these substances, 3-4 tea spoons, need to be taken to achieve an average reduction in LDL-C of between 7 and 10.5%. This is an issue as plant sterols and stanols are expensive.

Therefore there has also been increasing interest in non-drug therapies such as probiotics to improve blood cholesterol profiles. A number of studies have identified the role of bile acids as signalling molecules in regulating lipid, glucose, and energy metabolism. Bile acids transport dietary fat and cholesterol into the circulation. The use of microbial strains in the reduction of cholesterol levels by regulating bile acid regulators is known. Bile Salt Hydrolase (BSH) active probiotics have been shown to increase intraluminal bile acid deconjugation, resulting in increased levels of circulating deconjugated bile salts in humans and animal studies. As bile acids are deconjugated in the intestines, dietary and biliary cholesterol absorption is reduced and the recirculation of bile is altered, resulting in better control of (LDL-C) levels in blood. A number of studies have tested and shown the lipid lowering effects of a probiotic in commercial yoghurts.

In WO2015/067947, *Lactobacillus plantarum* strains have been suggested as BSH active probiotics with high upper gastrointestinal survival characteristics.

It is an object of the present invention to provide an improved or alternative treatment for high cholesterol. It is also an object to provide a method of treating, preventing or otherwise controlling cholesterol levels in an individual. It is a further object of the present invention to provide a probiotic composition which can be employed to reduce cholesterol levels in an individual.

SUMMARY OF THE INVENTION

In a first aspect of the present invention, there is provided a composition comprising *Lactobacillus plantarum* 2830 (ECGC 13110402), or mutant strain or strains thereof, for use in the reduction or modulation of total cholesterol (TC) and low density lipoprotein cholesterol (LDL-C) levels in an individual.

In a second aspect of the present invention, there is provided A composition comprising *Lactobacillus plantarum* 2830 (ECGC 13110402), or mutant strain or strains thereof, for use in the management, treatment or prevention of elevated total cholesterol (TC) and low density lipoprotein cholesterol (LDL-C) levels in an individual.

In a third aspect of the present invention, there is provided a composition comprising *Lactobacillus plantarum* 2830 (ECGC 13110402), or mutant strain or strains thereof, for use in the management, treatment or prevention of hypercholesterolaemia in an individual.

In a fourth aspect of the present invention, there is provided *Lactobacillus plantarum* 2830 (ECGC 13110402) for use in the manufacture of a medicament for the treatment or prevention of hypercholesterolaemia.

In a fifth aspect of the present invention, there is provided *Lactobacillus plantarum* 2830 (ECGC 13110402) in a method of treatment or prevention of hypercholesterolaemia.

In a sixth aspect of the present invention, there is provided *Lactobacillus plantarum* 2830 (ECGC 13110402) for use in the manufacture of a food supplement or foodstuff for management, treatment or prevention of hypercholesterolaemia In relevant aspects, it is preferred that the hypercholesterolaemia is mild hypercholesterolaemia.

Preferably, *Lactobacillus plantarum* 2830 (ECGC 13110402) will be administered to an individual in an amount in the range of $10^5$ cfu to $10^{12}$ cfu. More preferably, *Lactobacillus plantarum* 2830 (ECGC 13110402) may be in an amount in the range of $10^8$ cfu to $10^{10}$ cfu. Although it will be appreciated that different dosages may be administered depending upon the individuals' condition. Most preferably, the *Lactobacillus plantarum* is in an amount of about 120 mg of the active strain providing about $1.8 \times 10^9$ cfu.

The composition may comprise further excipients necessary for the manufacture of a dosage form and its breakdown following ingestion. The composition may further comprise disintegrants, binders, lubricants and glidants.

The composition may further comprise one or more disintegrants selected from: polyvinylpyrollidone, sodium starch glycolate and carboxymethylcellulose.

The composition may further comprise one or more binders selected from; starches, saccharides, cellulose, sugar alcohols, gelatin, polyvinylpyrollidone and polyethylene glycol. Preferably the composition further comprises corn starch.

The composition may further comprise one or more glidants selected from talc, magnesium carbonate, fumed silica and silicon dioxide. Preferably the composition further comprises silicon dioxide.

The composition may further comprise one or more lubricants selected from stearic acid, vegetable stearin and magnesium stearate. Preferably the composition further comprises magnesium stearate.

Administration frequency would also be dependent upon an individuals' condition but preferably the composition would be administered twice daily.

The composition may be administered at any time of day. However, preferably the composition is adminstered before meals.

It will be apparent to the skilled addressee that the composition may be in any easily administered form, for example in the form of a powder, tablet, or capsule. Alternatively, the composition may be in the form of a food stuff or food additive. The composition may be in the form of a drinkable liquid, a spread and/or powder which can be mixed with a solid or liquid food stuff. The composition could be used as a dietary supplement—for example to be blended with foods/drinks or consumed alongside foods/drinks.

The composition may further comprise an excipient or carrier compound to modify the release profile of one or more of the components through the intestinal environment. Release should occur at the most appropriate time for reducing cholesterol absorption. Typically, the culture must survive relatively intact until it reaches the intestinal enterocytes of the small intestine.

The composition may be encapsulated. Many encapsulation techniques will be apparent to the skilled addressee and the one employed will be tailored to the required stability of *Lactobacillus plantarum* 2830 (ECGC 13110402) during digestive transit.

*Lactobacillus plantarum* 2830 (ECGC 13110402) may be concentrated and/or freeze dried. Advantageously *Lactobacillus plantarum* 2830 (ECGC 13110402) has demonstrated excellent freeze drying survival in pilot scale manufacturing trials.

The composition may further comprise one or more active ingredients selected from: vitamins, minerals, phytochemicals, antioxidants, and combinations thereof.

Vitamins may include fat soluble vitamins such as vitamin A, vitamin D, vitamin E, and vitamin and combinations thereof. In some embodiments, vitamins can include water soluble vitamins such as vitamin C (ascorbic acid), the B vitamins (thiamine or B1, riboflavin or B25 niacin or B3, pyridoxine or B6, folic acid or B9, cyanocobalimin or B12, pantothenic acid, biotin), and combinations thereof.

Minerals may include, but are not limited to, sodium, magnesium, chromium, iodine, iron, manganese, calcium, copper, fluoride, potassium, phosphorous, molybdenum, selenium, zinc, and combinations thereof.

Antioxidants may include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

Phytochemicals may include but are not limited to cartotenoids, chlorophyll, chlorophyllin, fiber, flavonoids, anthocyamns, cyaniding, delphinidin, malvidin, pelargonidin, peonidin, petunidin, flavanols, catechin, epicatechin, epigallocatechin, epigailocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

The composition may comprise a prebiotic specifically tailored to *Lactobacillus plantarum* 2830 (ECGC 13110402). The prebiotic may selectively accentuate the growth and survivability of *Lactobacillus plantarum* 2830 (ECGC 13110402).

The composition may further comprise one or more fillers. The composition may further comprise one or more fillers selected from the following: maltodextrin, sucrose or fillers with cholesterol reducing ability. Preferably the composition further comprises beta glucans which can reduce cholesterol thus cooperatively enhancing the cholesterol reducing/controlling functions of the other excipients in the composition.

The composition may be administered with one or more statins, sterols and/or stanols. Advantageously co-administration with known cholesterol lowering therapeutics can provide enhanced cholesterol reduction and/or control. Plant sterols have been shown to increase levels of serum plant sterols which have been found part of atherosclerotic plaques and in the retina of long-term plant sterol and stanol users. BSH-active probiotic bacteria have been shown to reduce circulating cholesterol and plant sterols. A combination of plant sterols and BSH-active probiotics can therefore reduce/control cholesterol levels and reduce plant sterol serum levels advantageously improving the safety profile of sterol products. Mechanistically BSH-active bacteria should work in a complementary fashion with statins to amplify LDL receptor activity and the clearance of serum cholesterol, as they increase bile salt deconjugation and reduce sterol absorption. Therefore co-administration of BSH-active probiotics and statins can potentially result in a greater reduction in serum LDL-C enabling a reduction in statin dosage thus reducing costs and side effects and improving patient compliance.

Preferably the composition is stored at 4° C. or below. Bacterial growth is stabilised in this temperature range thus ensuring the stability of the composition.

The composition may further comprise a prebiotic growth medium which is specific to the growth of the *Lactobacillus plantarum* strain. The prebiotic growth medium will preferably be capable of being producing by the *Lactobacillus plantarum* strain by reverse enzyme reaction. The enzyme may comprise a saccharolytic or glycosidase enzymes. These saccharolytic or glycosidase enzymes may be derived from bacteria or fungi.

The prebiotic growth medium may comprise oligosaccharides such as galacto-oligosacharides, (GOS), gluco-oligosacharides, or fructo-oligosaccharides (FOS) in varying concentrations. It is preferred that the oligosaccharide form is substantially the same as the form produced by $\beta$-galactosidases, $\alpha$-galactosidases, $\alpha$- and $\beta$-glucosidases, $\alpha$-mannosidases and $\beta$-xylosidases reverse reactions of the strain.

The prebiotic growth medium may be present in an amount which provides optimal growth and survival of the strain within the gut without impacting on safety, tolerance, and shelf life.

In accordance with a further aspect of the present invention, there is provided *Lactobacillus plantarum* 2830 (ECGC 13110402), or mutant strain or strains thereof, for use in a method of preventing, treating or modulating hypercholesterolaemia, wherein the *Lactobacillus plantarum* is administered in an amount in the range of $1 \times 10^5$ to $10^{12}$ cells twice a day.

More preferably, the *Lactobacillus plantarum* may be administered in an amount in the range of $1 \times 10^8$ to $1 \times 10^{10}$ cells. Most preferably, the *Lactobacillus plantarum* is administered in an amount about $1.8 \times 10^9$ cells. Also preferably, the *Lactobacillus plantarum* is administered in an amount of about 120 mg of the active strains.

The *Lactobacillus plantarum* may be administered shortly before, during or after morning and evening meals. Preferably, the *Lactobacillus plantarum* is administered shortly before breakfast and the evening meal.

The *Lactobacillus plantarum* may be administered as a medicine or as a dietary supplement.

The *Lactobacillus plantarum* may be in a freeze dried form.

The *Lactobacillus plantarum* may be administered with one or more additional cholesterol lowering components. Such components may comprises: statins, sterols and/or stanols. Furthermore, the *Lactobacillus plantarum* may be administered with one or more probiotics and/or prebiotics. The *Lactobacillus plantarum* may be administered in combination with a prebiotic growth medium which is specific to the growth of the *Lactobacillus plantarum* strain. The prebiotic growth medium will preferably be capable of being producing by the *Lactobacillus plantarum* strain by reverse enzyme reaction. The prebiotic growth medium may comprise oligosaccharides, which will preferably comprise galacto-oligosaccharide (GOS).

Preferably, the *Lactobacillus plantarum* is stored at 4° C. or below before administration.

In accordance with yet a further aspect of the present invention, there is provided a method of producing *Lactobacillus plantarum* 2830 (ECGC 13110402), or mutant strain or strains thereof, for use in the preparation of a medicament or food supplement, comprising:
 a) fermenting *Lactobacillus plantarum* under conditions sufficient to produce a culture broth;
 b) concentrating the *Lactobacillus plantarum* from the culture broth so as to form a concentrate of the *Lactobacillus plantarum* cells;
 c) subjecting the concentrate to a cryoprotectant so as to form a mixture; and
 d) freeze drying the mixture.

The survival rates for freeze drying the *Lactobacillus plantarum* cells by such a method is over 70%. Furthermore, the method has been advantageously found that the method produces the *Lactobacillus plantarum* cells in amounts of up to $8 \times 10^{11}$ cfu/g.

The method will of course be suitable for producing *Lactobacillus plantarum* 2830 (ECGC 13110402), or mutant strain or strains thereof, for a composition as herein above described, or indeed the *Lactobacillus plantarum* 2830 (ECGC 13110402) as herein above described.

It will be apparent to the skilled addressee that a number of the features of the composition listed in respect to a number of the aspects of the invention will be interchangeable with the composition administered in the present method.

DETAILED DESCRIPTION OF THE INVENTION

Embodiments of the present invention will now be described, by way of example only.

A human volunteer study was conducted to establish the safety, compliance and extent of cholesterol reduction and control by administering formulations comprising *Lactobacillus plantarum* ECGC 13110402 to 49 mildly hypercholesterolaemic adults. The study was carried out independently by the Department of Food and Nutritional Sciences at the University of Reading, UK. The study was carried out according to the Helsinki declaration and written informed consent was obtained from all volunteers. The study protocol was approved by the Research Ethics committee of the University of Reading.

Subjects were male or female, aged 30-65 years. Subjects were excluded if they had had a previous cardiovascular event within the last 6 months, if secondary dyslipemias related to thyroid dysfunction were present, if they had used any drug affecting lipid metabolism in the previous 3 months, if they had a history of alcohol abuse, if they had taken antibiotics in the previous 6 months or if they had taken prebiotics/probiotic preparations in the last month.

Those who met the inclusion criteria were screened prior to the commencement of the study. A baseline blood sample was taken and their BMI and blood pressure were measured. The screening blood sample was analysed for full blood count (FBC) and liver function tests (LFTs) to determine overall health. Total cholesterol (TC), low density lipoprotein cholesterol (LDL-C), high density lipoprotein cholesterol (HDL-C), fasting triacylglycerol (TAG) and vitamin D were also measured. Urine, blood and faeces were collected for bile acid and metagenomic and metabolomics studies.

The study was a single-centre, prospective, randomized, double-blind, placebo-controlled, parallel-group trial. Subjects were randomly distributed into two groups: placebo or treatment with *Lactobacillus plantarum* ECGC 13110402. The placebo and treatment groups were provided with a blister packed DR 1 capsule. The treatment group received 120 mg of active *Lactobacillus plantarum* ECGC 13110402 providing a dose of $1.8 \times 10^9$ cells per capsule which was administered once or twice daily; once at breakfast and once in the evening as a dietary supplement. Participants were advised not to change their regular diet or physical activity throughout the trial period. Habitual diet was assessed by pre-validated 5-day food diaries (2 weekend and 3 week days).

Formulation details for the active and placebo formulations respectively are shown in tables 1 and 2 below:

TABLE 1

| Ingredient | mg/capsule | Billion for capsule | g for production |
|---|---|---|---|
| Probiotic powder | 120 | $8.4 \times 10^9$ | 567.00 |
| Corn starch | 118.6 | | 560.39 |
| Magnesium stearate | 3.2 | | 15.12 |
| Silicon dioxide | 3.2 | | 15.12 |
| Capsule DR size 1 white | 75 | | 354.38 |
| TOTAL | 320 | | 1512 |

TABLE 2

| Ingredient | mg/capsule | Billion for capsule | g for production |
|---|---|---|---|
| Corn starch | 238.6 | | 1127.39 |
| Magnesium stearate | 3.2 | | 15.12 |
| Silicon dioxide | 3.2 | | 15.12 |
| Capsule DR size 1 white | 75 | | 354.38 |
| TOTAL | 320 | | 1512 |

Volunteers were pre-screened 2 weeks prior to the study start and were advised to refrain from any pre/probiotic intake. The study consisted of two phases: a treatment period (12 weeks) and a wash-out period (4 weeks). The study included a baseline visit at selection, a visit at the midpoint and at the endpoint of the treatment period (weeks 0, 6 and 12, respectively), and a fourth visit after the wash-out period (week 16).

An initial set of analyses examined the demographic and outcome variables at baseline to ensure that the two groups were well matched. Continuous variables were analysed using the unpaired t-test, whilst the Chi-square test was used for the categorical variables.

Study outcomes between the two study groups were analysed in terms of changes between timepoints. Four study periods were examined for changes in outcomes: baseline to midpoint (0-6 weeks), midpoint to endpoint (6-12 weeks), baseline to endpoint (0-12 weeks) and endpoint to washout (12-16 weeks). Data for each analysis was restricted to the particular two timepoints in the analysis. The analyses were performed using analysis of covariance (ANCOVA). The latter timepoint was used as the outcome variable, with the earlier timepoint considered as a covariate. This approach is mathematically preferable to simply comparing the change over time between groups, as it takes into account the variable starting values for the test and control group.

The first set of analyses considered all study participants and different patient subgroups. These subgroups were based on baseline total cholesterol (<5 mmol/l, 5-5.9 mmol/l and ≥6.0 mmol/l), gender and age (<50 yrs, 50-59 yrs, ≥60 yrs).

There were no safety, compliance, or tolerance issues reported by volunteers throughout the study. Three volunteers dropped out of the study due to antibiotic treatment for non related illnesses which excluded them from further study participation.

Volunteers were asked to fill in daily gastrointestinal symptom diaries throughout the duration of the study and to report any adverse effects experienced. GI symptoms for abdominal pain, bloating and flatulence were recorded by volunteers as none (0), mild (1), moderate (2) or severe (3). Average scores of self reported gastrointestinal (GI) symptoms from baseline to 12 weeks (Table 3) showed no significant difference in bowel movements per day or stool consistency (Bristol stool chart) between the groups. One volunteer in the active group reported moderate abdominal pain, bloating and flatulence, while in the placebo group two volunteers reported moderate flatulence. None of the study participants reported severe GI side effects during the baseline to 12 week treatment period and no significant differences in stool morphology and frequency were observed between treatment groups. All other volunteers reported no symptoms.

TABLE 3

|  | Placebo | | Active | |
| --- | --- | --- | --- | --- |
|  | Average | SD | Average | SD |
| Bowel movements | 1.28 | 0.53 | 1.27 | 0.51 |
| Stool consistency | 3.35 | 1.25 | 3.55 | 0.90 |
| Abdominal pain | 0.15 | 0.18 | 0.32 | 0.47 |
| Bloating | 0.28 | 0.31 | 0.35 | 0.49 |
| Flatulence | 0.68 | 0.44 | 0.53 | 0.48 |

The baseline characteristics (total cholesterol, anthropometric measurements, systolic and diastolic pressure) were compared between the placebo (n=23) and active (n=23) groups and are shown in table 4 below. The results suggested no significant difference between the two study groups in terms of their demographics (age, sex) or for any of the lipid or anthropometric measures at baseline.

TABLE 4

| Variable | Placebo (n = 23) Mean (SD) | Active (n = 23) Mean (SD) | P-value |
| --- | --- | --- | --- |
| Age | 52.0 (8.4) | 52.3 (10.7) | 0.89 |
| Gender: Female | 14 (61%) | 18 (78%) | 0.20 |
| Gender: Male | 9 (39%) | 5 (22%) |  |
| Total cholesterol | 5.22 (0.92) | 5.10 (0.71) | 0.62 |
| HDL cholesterol | 1.24 (0.31) | 1.40 (0.35) | 0.10 |
| LDL cholesterol | 3.44 (0.76) | 3.20 (0.68) | 0.28 |
| Triacylglycerides | 1.18 (0.45) | 1.11 (0.46) | 0.61 |
| Weight | 79.2 (16.5) | 72.1 (12.0) | 0.10 |
| BMI | 26.8 (5.0) | 26.7 (3.7) | 0.96 |
| Waist | 92.3 (13.5) | 89.6 (12.0) | 0.49 |

Independent statistical analysis was performed to examine how the changes in lipid measurements over the course of the study varied between the two study groups. Changes between four pairs of time points (0-6 weeks; 0-12 weeks; 6-12 weeks; 12-16 weeks) were examined. Only analysis of data between baseline and end of treatment (0-12 week) is shown unless otherwise indicated. Clinically or statistically significant variations between other timepoints are highlighted. These are summarised in Tables 3-5.

Tables 5-7 show the mean and standard deviation at baseline and the end of treatment at 12 weeks. Table 5 shows the changes in lipid measurements for all subjects (n=46) from baseline to 12 weeks. Table 6 shows the changes in lipid measurements for subjects with TC of <5 mmol/l (n=23) from baseline to 12 weeks. Table 7 shows the changes in lipid measurements for subjects with TC of 5-5.9 mmol/l (n=17) from baseline to 12 weeks. Analyses was carried out for 6.0+mmol/l but as this group only contained 6 subjects (3 active, 3 placebo) only statistically significant differences are reported, with appropriate caveats.

The group differences from the ANCOVA analyses are reported, with the mean difference and corresponding confidence interval. These are reported as outcome for active group minus outcome for placebo group adjusting for the baseline value. P-values indicating the significance of the results are reported.

TC, LDL-C, HDL-C and TAG concentrations are expressed in mmol/l.

The groups were stratified according to baseline cholesterol levels as shown in tables 5-7 and according to age (<50 years n=16; 50-59 years n=18; ≥60 years, n=12) and gender (female=32, male n=14).

TABLE 5

| Outcome | Group | Baseline Mean (SD) | 12 weeks Mean (SD) | Change Mean (SD) [range] | % Change Mean (SD) [range] | Group Difference Mean (95% CI) | P-value |
| --- | --- | --- | --- | --- | --- | --- | --- |
| TC | Placebo | 5.22 (0.92) | 5.33 (0.84) | 0.11 (0.66) [−1.0, 1.4] | 3.1 (13.4) [−14.6, 34.1] | 0 | 0.51 |
|  | Active | 5.10 (0.71) 5.16 | 5.12 (0.87) | 0.02 (0.56) [−1.3, 1.2] | 0.6 (10.5) [−22.4, 23.3] | −0.12 (−0.47, 0.24) −2.3% |  |
| HDL | Placebo | 1.24 (0.31) | 1.24 (0.29) | 0.00 (0.17) [−0.2, 0.5] | 1.5 (17.0) [−14.3, 62.5] | 0 | 0.23 |
|  | Active | 1.40 (0.35) 1.32 | 1.46 (0.42) | 0.06 (0.15) [−0.1, 0.5] | 3.4 (10.5) [−12.5, 33.3] | 0.06 (−0.04, 0.16) +4.5% |  |
| LDL | Placebo | 3.44 (0.76) | 3.54 (0.70) | 0.10 (0.62) [−0.9, 1.3] | 4.9 (19.5) [−22.9, 52.0] | 0 | 0.15 |
|  | Active | 3.20 (0.69) 3.32 | 3.13 (0.78) | −0.07 (0.53) [−1.3, 1.0] | −1.4 (15.6) [−36.4, 26.3] | −0.24 (−0.56, 0.09) −7.2% |  |
| TAG | Placebo | 1.18 (0.45) | 1.20 (0.39) | 0.03 (0.41) [−0.9, 0.6] | 10.9 (35.7) [−52.9, 83.3] | 0 | 0.96 |
|  | Active | 1.11 (0.46) 1.14 | 1.15 (0.65) | 0.04 (0.36) [−0.5, 0.8] | 3.6 (34.8) [−55.6, 114.3] | 0.01 (−0.22, 0.23) +0.8% |  |

TABLE 6

| Outcome | Group | Baseline Mean (SD) | 12 weeks Mean (SD) | Change Mean (SD) [range] | % Change Mean (SD) [range] | Group Difference Mean (95% CI) | P-value |
|---|---|---|---|---|---|---|---|
| TC | Placebo | 4.50 (0.28) | 4.79 (0.43) | 0.29 (0.60) [−0.7, 1.4] | 7.1 (13.7) [−14.6, 34.1] | 0 | 0.31 |
| | Active | 4.53 (0.33) 4.51 | 4.61 (0.42) | 0.08 (0.38) [−0.5, 1.0] | 2.0 (8.5) [−10.9, 23.3] | −0.19 (−0.56, 0.19) −4.2% | |
| HDL | Placebo | 1.09 (0.28) | 1.11 (0.23) | 0.02 (0.19) [−0.2, 0.5] | 4.5 (22.3) [−14.3, 62.5] | 0 | 0.33 |
| | Active | 1.34 (0.30) 1.21 | 1.44 (0.42) | 0.10 (0.19) [−0.1, 0.5] | 6.2 (12.9) [−12.5, 33.3] | 0.09 (−0.10, 0.27) +7.4% | |
| LDL | Placebo | 2.88 (0.33) | 3.15 (0.47) | 0.26 (0.59) [−0.8, 1.3] | 10.5 (21.0) [−22.9, 52.0] | 0 | 0.03 |
| | Active | 2.71 (0.31) 2.79 | 2.72 (0.28) | 0.02 (0.30) [−0.6, 0.6] | 1.3 (11.7) [−21.4, 26.1] | −0.39 (−0.74, −0.04) −13.9% | |
| TAG | Placebo | 1.14 (0.51) | 1.15 (0.38) | 0.02 (0.41) [−0.9, 0.5] | 12.3 (37.3) [−52.9. 62.5] | 0 | 0.96 |
| | Active | 1.08 (0.39) 1.12 | 0.97 (0.35) | −0.12 (0.25) [−0.5, 0.2] | −8.1 (25.4) [−55.6, 28.6] | −0.01 (−0.22, 0.23) −0.9% | |

TABLE 7

| Outcome | Group | Baseline Mean (SD) | 12 weeks Mean (SD) | Change Mean (SD) [range] | % Change Mean (SD) [range] | Group Difference Mean (95% CI) | P-value |
|---|---|---|---|---|---|---|---|
| TC | Placebo | 5.48 (0.25) | 5.52 (0.64) | 0.04 (0.74) [−0.8, 1.2] | 1.1 (13.8) [−14.5, 22.2] | 0 | 0.44 |
| | Active | 5.55 (0.24) 5.51 | 5.25 (0.54) | −0.30 (0.64) [−1.3, 0.6] | −5.2 (11.4) [−22.4, 11.8] | −0.23 (−0.87, 0.40) −4.17% | |
| HDL | Placebo | 1.30 (0.26) | 1.31 (0.33) | 0.01 (0.15) [−0.2, 0.2] | 0.3 (11.2) [−12.5, 15.4] | 0 | 0.91 |
| | Active | 1.50 (0.47) 1.4 | 1.51 (0.49) | 0.01 (0.1) [−0.1, 0.2] | 0.6 (6.4) [−8.3, 11.8] | −0.01 (−0.15, 0.14) −0.01 | |
| LDL | Placebo | 3.61 (0.27) | 3.63 (0.54) | 0.02 (0.67) [−0.8, 1.1] | 1.5 (19.2) [−21.1, 33.3] | 0 | 0.11 |
| | Active | 3.55 (0.40) 3.58 | 3.16 (0.58) | −0.39 (0.65) [−1.3, 0.6] | −10.2 (18.3) [−36.4, 18.8] | −0.47 (−1.08, −0.13) −13.1% | |
| TAG | Placebo | 1.24 (0.42) | 1.29 (0.48) | 0.04 (0.46) [−0.9, 0.6] | 10.7 (39.3) [−52.9. 83.3] | 0 | 0.56 |
| | Active | 1.11 (0.58) 1.17 | 1.26 (0.92) | 0.15 (0.38) [−0.3, 0.7] | 5.9 (26.4) [−33.3, 41.2] | 0.13 (−0.33, 0.58) +11.1% | |

Total cholesterol (TC) from baseline to 12 weeks was reduced in all groups compared to the placebo group (Tables 5-7). The baseline adjusted value for TC levels in all subjects was 0.12 mmol/l lower in the active group compared to the placebo group, a 2.3% decrease. Stratification according to baseline TC concentrations revealed variations between the higher TC and medium to low subgroups. In the TC <5.0 mmol/l subgroup the change between baseline and end of treatment was 4.2% lower in the active compared to the placebo group (0.19 mmol/l lower). Similarly in the TC 5-5.9 mmol/l group, the baseline adjusted end of treatment TC concentrations were 0.23 mmol/l lower in the active group, corresponding to a 4.17% reduction. In the TC ≥6.0 mmol/l (0-6 weeks) group a statistically significant reduction in TC of 2.44 mmol/l was observed, corresponding to a 36.7% reduction (P=0.045) (data not shown in tables 5-7). However, the size of this group was very small (n=3 placebo/3 active) and so despite its statistical significance no group relevance should be attributed to this effect. No significant effect of gender on TC was identified. Although most results were not of statistical significance, there was a common group trend for a decrease in TC in the active treatment groups when compared to the placebo. The results also suggested that patients with higher initial levels of TC may benefit from higher reductions in TC than others.

HDL-C increased slightly between baseline and 12 weeks for both placebo and active groups. On adjusting for variable baselines the HDL-C concentrations for the all subject and TC <5 mmol/l group were 0.06 mmol/l (4.5%) and 0.09 mmol/l (7.4%) higher in the active group when compared to the placebo. Most of this difference occurred in the 6-12 week period where differences approaching statistical significance were seen for both all subject (p=0.06) and TC <5 mmol/l groups (p=0.09). The all subject and TC <5 mmol/l groups in this period showed average increases in HDL cholesterol levels of 0.09 mmol/l (6.5%) and 0.10 mmol/l (7.8%) respectively when compared to the placebo group.

Age stratification revealed statistically significant group differences (p=0.03) in the 60+ group (n=12) who had average increases in HDL cholesterol of 0.23 mmol/l (+14.7%) when compared to the placebo group. Stratification according to baseline TC concentrations and gender revealed no significant treatment effect on HDL levels.

LDL-C cholesterol reduced between baseline and 12 weeks in all the active treatment groups. This effect was not observed in the placebo group.

Upon adjusting for variable baselines, LDL-C concentrations for the all subject groups were on average 0.24 mmol/l (7.2%) lower when compared to placebo. LDL-C concentrations in the TC <5.0 mmol/l group were significantly lower by 0.39 mmol/l (13.9%) in the active compared to the placebo group (P=0.03). These reductions have clinical and commercial significance. In the TC 5.0-5.9 mmol/l group, LDL-C showed an average 0.47 mmol/l decrease (13.1%), but this did not reach statistical significance. The LDL reducing effect appeared to occur consistently across both the 0-6 and 6-12 week periods. The results suggest patients with higher initial levels of LDL cholesterol may benefit from higher reductions in LDL-C than others.

Stratification according to gender revealed a more pronounced LDL-C reducing effect in female volunteers compared to males (p=0.06). Active group concentrations were 0.41 mmol/l (12.4%) lower for females compared to placebo while a 0.06 mmol/l (1.8%, P=0.06) increase was observed for the active male group compared to placebo (P=0.83).

Stratification according to age showed higher decreases in LDL-C concentrations with increasing age. Only slight changes were observed in the baseline adjusted LDL-C concentrations in the <50 years group (0.08 mmol/l increase). LDL-C decreases were more pronounced in the 50-59 group (0.49 mmol/l) and in the ≥60 years group (0.31 mmol/l), corresponding to a 15% and 9.14% decrease respectively in the active group compared to the placebo.

No significant effects on triacylgyceride concentrations were observed upon the ingestion of either the active or placebo treatments in the all subjects, TC=<5 mmol/l, or TC 5-5.9 mmol/l groups. Age stratification showed a statistically significant (p=0.002) triglyceride reduction in the 60+ group of 0.48 mmol/l (53.9%) between the placebo and active group. This large reduction in triglycerides was consistent across all testing time periods with a statistically significant reduction (p=0.03) of 0.26 mmol/l (32.9%) in the 6-12 week period and a reduction of 0.28 mmol/l (31.4%, p=0.07) in the baseline to 6 week period.

Changes in anthropometric measurements for all subjects (n=46) in the placebo and active treatment groups are shown from the baseline to the end of treatment after 12 weeks in table 8 below. The mean values and standard deviation for each measured outcome at baseline and after 12 weeks are shown in table 8. Group differences from the ANCOVA analyses are also shown with the mean difference and corresponding confidence interval. These are reported as outcome for active group minus outcome for placebo group adjusting for the baseline value. P-values indicating the significance of the results are reported. Body weight is expressed in kg, BMI in kg/m$^2$ and waist circumference in cm.

activities were performed: a) flask tests conducted to check different hypoallergenic media; b) fermentations of 1-5 L, concentration and freeze drying of small amounts to study; c) testing different cryoprotectants; d) testing different freeze drying curves; e) fermentation in 80 L, concentration and freeze drying. The final step was a production in a 80 L fermenter which resulted in: (i) cell count >8×10$^{11}$ cfu/g; (ii) Aw: 0.11; (iii) a quantity of 700 g of concentrated biomass, freeze dried and not diluted/standardized with any excipient. Therefore, this particular strain looked extremely promising from a manufacturing point of view. Survival rate of the cells was found to be at more than 70% and yields were at 1.25% which is extremely high.

The forgoing embodiments are not intended to limit the scope of the protection afforded by the claims, but rather to describe examples of how the invention may be put into practice.

The invention claimed is:

1. A composition comprising *Lactobacillus plantarum* 2830, deposited at the European Collection of Cell Cultures under Accession Number 13110402, for use in the management or treatment of elevated total cholesterol (TC) and low density lipoprotein cholesterol (LDL-C) levels, or hypercholesterolaemia, in an individual, wherein the *Lactobacillus plantarum* 2830 is freeze dried and either:
   (i) the composition further comprises an excipient or a carrier compound;
   (ii) the composition is encapsulated; or
   (iii) the *Lactobacillus plantarum* 2830 is concentrated.

TABLE 8

| Outcome | Group | Baseline Mean (SD) | 12 weeks Mean (SD) | Change Mean (SD) [range] | % Change Mean (SD) [range] | Group Difference Mean (95% CI) | P-value |
|---|---|---|---|---|---|---|---|
| Weight | Placebo | 79.2 (16.5) | 79.3 (16.8) | 0.2 (1.7) [−2.6, 3.5] | 0.1 (2.1) [−3.3, 4.7] | 0 | 0.18 |
| | Active | 72.1 (12.0) | 72.8 (12.6) | 0.7 (1.7) [−2.6, 3.8] | 0.9 (2.2) [−2.8, 4.9] | 0.7 (−0.3, 1.7) | |
| BMI | Placebo | 26.8 (5.0) | 27.0 (5.2) | 0.3 (1.3) [−3.1, 4.2] | 0.9 (4.7) [−9.3, 15.5] | 0 | 0.41 |
| | Active | 26.7 (3.7) | 27.2 (4.0) | 0.5 (0.9) [−1.1, 3.3] | 2.0 (3.3) [−3.9, 11.8] | 0.3 (−0.4, 1.0) | |
| Waist | Placebo | 92.3 (13.5) | 90.5 (13.8) | −1.8 (6.4) [−14, 12] | −1.8 (6.8) [−17.3, 12.9] | 0 | 0.61 |
| | Active | 89.6 (12.0) | 89.1 (11.0) | −0.5 (5.7) [−13, 13] | −0.2 (6.7) [−13.0, 16.3] | 0.9 (−2.6, 4.4) | |

No significant changes were noted in the anthropometric parameters relevant to weight, BMI and waist circumference between baseline and end of treatment at 12 weeks.

The results show that *Lactobacillus plantarum* ECGC 13110402 has the potential to lower blood TC and LDL-C in hypercholesterolaemic and mildly hypercholesterolaemic subjects.

Active *Lactobacillus plantarum* ECGC 13110402 and placebo capsules were stored at 4° C. throughout the study duration. Product stability was checked at baseline, 6 weeks and 12 weeks (end of treatment) of the study and no significant change was observed in bacterial numbers. No bacterial growth was detected in the placebo capsules.

Analysis of safety parameters did not show deleterious effects of consuming *Lactobacillus plantarum* ECGC 13110402. *Lactobacillus plantarum* is a widely used probiotic which is considered Generally Regarded as Safe (GRAS) by the US Food and Drug Administration (FDA) and has a Qualified Presumption of Safety (QPS) designation by the European Food Standard Agency. This would suggest that *Lactobacillus plantarum* ECGC 13110402 has the potential to be a safe and effective treatment for the treatment of hypercholesterolemia.

Industrial scale-up experiments were also conducted on *Lactobacillus plantarum* ECGC 13110402. The following 2. The composition of claim 1, wherein the *Lactobacillus plantarum* 2830 is present in an amount in the range of 1×10$^5$ to 1×10$^{12}$ cells.

3. The composition of claim 2, wherein the *Lactobacillus plantarum* 2830 is present in an amount in the range of 1×10$^8$ to 1×10$^{10}$ cells.

4. The composition of claim 3, wherein the *Lactobacillus plantarum* 2830 is present in an amount of about 120 mg in the composition providing about 1.8×10$^9$ cells.

5. The composition of claim 1, further comprising one or more of the following: corn starch, magnesium stearate and silicon dioxide.

6. The composition of claim 1 formulated for oral administration to said individual twice daily.

7. The composition of claim 1, wherein the composition further comprises one or more active ingredients selected from the group consisting of vitamins, minerals, phytochemicals, antioxidants, filler materials, and combinations thereof.

8. The composition of claim 7, wherein the filler materials comprise one or more of the following: maltodextrin, sucrose or fillers with cholesterol reducing ability.

9. The composition of claim 8, wherein the filler material comprises beta glucans.

10. The composition of claim 1, further comprising one or more of the following: statins, sterols and/or stanols.

11. The composition of claim 1, further comprising a prebiotic growth medium which is specific to the *Lactobacillus plantarum* 2830 strain.

12. The composition of claim 11, wherein the prebiotic growth medium is capable of being produced by the *Lactobacillus plantarum* 2830 strain by an enzyme reaction catalyzed in reverse to produce said prebiotic growth medium.

13. The composition of claim 11, wherein the prebiotic growth medium comprises oligosaccharides.

14. The composition of claim 13, wherein the oligosaccharides comprise a galacto-oligosaccharide (GOS).

15. A composition comprising *Lactobacillus plantarum* 2830, deposited at the European Collection of Cell Cultures under Accession Number 13110402, for use in a method of treating or modulating hypercholesterolaemia in an individual, wherein the *Lactobacillus plantarum* 2830 is formulated for oral administration in an amount in the range of $1 \times 10^5$ to $10^{12}$ cells once or twice a day, and wherein the *Lactobacillus plantarum* 2830 is in a freeze dried form, and optionally the composition further comprises one or more cholesterol lowering agents.

16. The composition of claim 15, wherein the *Lactobacillus plantarum* 2830 is for administration in said individual shortly before, during or after morning and evening meals.

17. The composition of claim 16, wherein the *Lactobacillus plantarum* 2830 is for administration in said individual shortly before breakfast and the evening meal.

18. The composition of claim 17, wherein the *Lactobacillus plantarum* 2830 is formulated in the form of a dietary supplement.

* * * * *